United States Patent [19]

Fujii et al.

[11] 4,425,335

[45] Jan. 10, 1984

[54] ESTER DERIVATIVES OF ALKOXYBENZOYLDEOXYFLUOROURIDINE

[75] Inventors: Setsuro Fujii, Toyonaka; Bompei Yasui, Ikoma; Mitsuo Nakamura, Kyoto; Mitsuru Hirohashi, Ikoma; Tomohisa Miyamoto, Settsu; Kazuko Ando, Hirakata; Iwao Hashimoto; Naoki Umeda, both of Osaka; Masahiro Kawasaki, Kashihara, all of Japan

[73] Assignee: Funai Yakuhin Kogyo Kabushiki Kaisha, Osaka, Japan

[21] Appl. No.: 291,809

[22] Filed: Aug. 10, 1981

[30] Foreign Application Priority Data

Sep. 11, 1980 [JP] Japan .............................. 55-126776

[51] Int. Cl.$^3$ ...................... A61K 31/70; C07H 19/08
[52] U.S. Cl. ...................................... 424/180; 536/23
[58] Field of Search .......................... 536/23; 424/180

[56] References Cited

U.S. PATENT DOCUMENTS 3,853,845  12/1974  Rousseau et al. ..................... 536/23

FOREIGN PATENT DOCUMENTS 9882  4/1980  European Pat. Off. .
2025401  1/1980  United Kingdom .

OTHER PUBLICATIONS

Carter et al., *New Drugs in Cancer Chemotherapy*, pp. 1–2 (1981).
Halnan, *Treatment of Cancer*, p. 80 (1982).
Hoshi et al., *Farumashia*, vol. 9, No. 7, pp. 464–468 (1973) and English translation of pertinent portions.
Oslo, *Remington's Pharmaceutical Sciences*, 16th Ed., pp. 1081–1082, Chapter 62 (1980).
Nodine et al., *Animal and Clinical, Pharmacologic Techniques in Drug Evaluation*, p. 632 (1964).
Dukes, *Side Effects of Drugs Annual I*, p. 336 (1977).
Holland et al., *Cancer Medicine*, pp. 675-675 (1973).

Laurence et al., *Evaluation of Drug Activities: Pharmacometrics*, vol. 2, p. 842 (1964).
Siegler et al., *Animal and Clinical, Pharmacologic Techniques in Drug Evaluation*, vol. 2, pp. 830, 834 (1967).
Oslo et al., *The United States Dispensatory*, 27th Ed., pp. 377–378, 527–528 (1973).
Baker et al., *Physicians' Desk Reference*, 32nd Ed., p. 1387 (1978).
Grollman et al., *Pharmacology and Therapeutics*, pp. 669–670 (1970).

*Primary Examiner*—Blondel Hazel
*Attorney, Agent, or Firm*—Birch, Stewart, Kolasch & Birch

[57] ABSTRACT

New ester derivatives of alkoxybenzoyldeoxyfluorouridine of the general formula

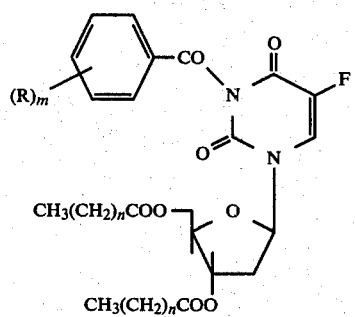

wherein R stands for an alkoxy group having 1 to 4 carbon atoms, m for 1 or 2, and n for 3 or 4 with the proviso that when m is 2, the adjacent two R's may be combined to form an alkylenedioxy group as a whole. These derivatives are prepared by acylating a 2'-deoxy-3',5'-di-O-alkylcarbonyl-5-fluorouridine with corresponding benzoyl halides and are useful as active ingredients for anti-tumor agents, especially for oral administration.

15 Claims, No Drawings

ESTER DERIVATIVES OF ALKOXYBENZOYLDEOXYFLUOROURIDINE

BACKGROUND AND SUMMARY OF THE INVENTION

The present invention relates to new ester derivatives of alkoxybenzoyldeoxyfluorouridine of the general formula:

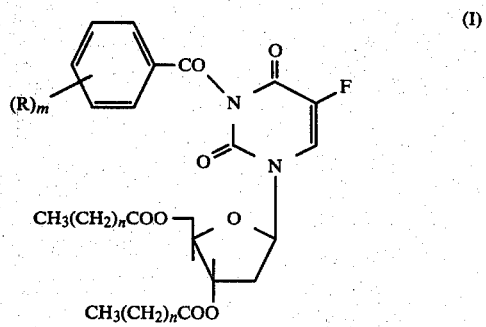

wherein R stands for an alkoxy group having 1 to 4 carbon atoms, m for 1 or 2, and n for 3 or 4 and when m is 2, the adjacent two R's may be combined to form an alkylenedioxy group as a whole. The present invention further relates to a process for the preparation of the ester derivatives and anti-tumor agents containing the ester derivatives as an active ingredient.

2'-Deoxy-5-fluorouridine (referred to hereinafter as FUDR) has been used as an anti-tumor agent but this compound is exceptionally high in toxicity for use as a medication and thus has a narrow safety region. In addition, this compound has considerable limitations in actual therapeutic applications since the mode of administering this compound is limited only to intraarterial injection, or in other words, this compound cannot be administered orally [Physicians' Desk Reference, p. 1387 (1978)]. 2'-Deoxy-3',5'-di-O-acetyl-5-fluorouridine (referred to hereinafter simply as acetyl-FUDR) is also known as one of the FUDR derivatives. However, this compound is evaluated as being almost equivalent in anti-tumor activity to FUDR and rather poor in effectiveness [Biochem. Pharmacology, 14, 1605 et seq., (1965); Cancer Research, 23, 420 et seq. (1963)].

3',5'-Dialkyl esters of FUDR are also reported as derivatives of FUDR [Biochem. Pharmacology, 14, 1605-1619 (1965), ibid. 15, 627-644 (1966)]. However, no compound was found which was satisfactory with respect to anti-tumor activity and toxicity. Recently, reported FUDR and acetyl-FUDR derivatives are such compounds wherein the hydrogen atom bonded to the nitrogen atom at the 3-position on the uracil ring is substituted by a specific aroyl group (U.K. Patent Appln. Ser. No. 2,025,401 published on Jan. 23, 1980 and European Patent Appln. Ser. No. 9,882 published on Apr. 16, 1980). However, further enhancement in anti-tumor activity is desired also in these compounds. Thus, there is a great demand for developing new FUDR derivatives which possess strong anti-tumor activity with weak toxicity and are suited for oral administration without the necessity of using troublesome intraarterial for intravenous injection.

As a result of extensive research made on a variety of FUDR derivatives for enhancing their anti-tumor activity and concurrently reducing their toxicity, it has now been surprisingly found that the new compounds of the general formula (1) are superior in anti-tumor activity to the known similar compounds at an equivalent toxicity level. The present invention has been accomplished on the basis of the above finding.

In the general formula (I), the alkoxy group having 1 to 4 carbon atoms represented by R may be a straight or branched chain alkoxy group such as methoxy, ethoxy, n-propoxy, isopropoxy, n-butoxy, isobutoxy, sec-butoxy, tert-butoxy and the like.

When two vicinal lower alkoxy groups exist as ring-substituents in the benzoyl group (R=a lower alkoxy group and m=2), the alkyl moieties of the two lower alkoxy groups may be combined to form an alkylene group. In this case, the two vicinal lower alkoxy group form an alkylenedioxy group as a whole. Preferable examples of the alkylenedioxy group include methylenedioxy, ethylenedioxy and propylenedioxy groups.

The new compounds of the general formula (I) of the present invention are prepared, for example, by reacting a 2'-dioxy-3',5'-di-O-alkylcarbonyl-5-fluorouridine of the general formula:

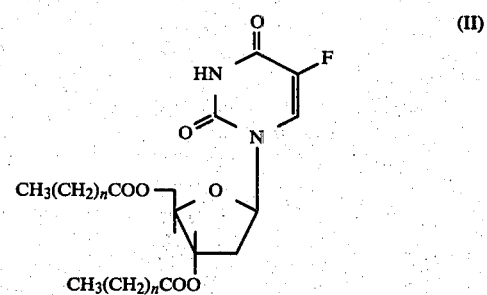

wherein n has the same meaning as given above, with a benzoyl halide of the general formula:

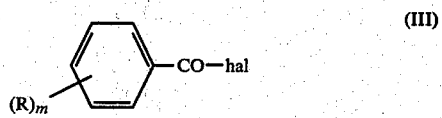

wherein R and m have the same meaning as given above and hal is a halogen atom.

The benzoyl chloride or bromide as a benzoyl halide of the starting material, is preferably used.

The benzoyl halide of the general formula (III) is preferably used in an amount of 1-3 molar proportion for the 2'-deoxy-3',5'-di-O-alkylcarbonyl-5-fluorouridine.

The reaction is preferably carried out as a rule in an organic solvent. Illustrative of the preferable organic solvents are aprotic solvents such as ether, dioxane, chloroform, ethyl acetate, acetonitrile, pyridine, dimethylformamide and the like.

The reaction is carried out normally in the presence of an organic base, especially aromatic amines such as pyridine, trialkylamines or N,N-dialkylanilines.

The organic base is used usually in an amount of 1-5 moles per mole of the benzoyl halide. As the organic bases per se may be used as the reaction medium, an excess amount of the organic base may be used in place of a part or all of the reaction solvent.

The reaction is carried out within a wide range of reaction temperatures, for example, under ice cooling or at a temperature up to the boiling point of the raction solvent used. As a rule, the reaction time is preferably within a period of from 30 minutes to 12 hours.

After completion of the reaction, the end product can be obtained by subjecting the reaction mixture directly to concentration under reduced pressure or by first filtering the reaction mixture and then concentrating the filtrate under reduced pressure, and finally recrystallizing the resultant residue or subjecting the residue to chromatography. When the end product is isolated as a viscous oily substance, it can be obtained as a solid form by dissolving the oily substance in a small amount of dimethylsulfoxide and slowly pouring the solution into water with agitation.

The products of the present invention possess high anti-tumor activity with weak toxicity as compared with the known similar FUDR derivatives. The pharmacological tests for the thus obtained compounds of the present invention were carried out as follows.

I. METHODS FOR TESTING (a) Pharmacological tests for measuring anti-tumor activity:

About 10,000,000 tumor cells of Sarcoma 180 (successively incubated for several generations in the peritoneal cavity of a male mouse of ICR strain) were transplanted subcutaneously into the inguinal region of 5 week-aged male mice of ICR strain. After the lapse of 24 hours, administration of the compounds of the present invention was started. The administration of the compounds of the invention was forcibly made orally once a day for 7 days. The body weight of each testing animal was measured every day just before the administration. The compounds of the invention, dissolved in polyethylene glycol 400, were administered to each testing animal while polyethylene glycol 400 alone as a placebo was administered to a control group of the animals. In each case, the same volume of 0.1 ml/10 g (body weight) was administered to each animal. Although the exact doses of the compounds of the invention varied depending on the particular compounds utilized, the doses were approximately within a range of from 0.5 mg/kg to 80 mg/kg. The doses were graded into 3–12 ranks for each testing compound. At each rank, the compound of the invention was administered to a group consisting of 6 mice while the placebo was administered to a control group consisting of 18 mice.

On the 8th day from the transplantation of the tumor cells, each mouse was put to death by bleeding under ether anethesia. After the tumor tissue was excised, its weight was immediately measured and recorded. An average value of tumor weights in the treated group (referred to as T) for each test compound and for each dose and an average value of tumor weights in the control group (referred to as C) were respectively calculated, to estimate a dose corresponding to T/C value of 0.70 or 0.50 for each test compound.

Concerning evaluation of the anti-tumor activity, a T/C value within the range of 0.70–0.51 is regarded to be moderately effective, while a value of less than 0.50 is regarded to be effective [Ohyo-Yakuri, 7, 1277–1292 (1973)]. Accordingly, the anti-tumor activity becomes stronger as the value indicating 0.70 or 0.50 becomes smaller.

(b) Test for measuring toxicity:

Judging from the effects achieved by the compounds of the present invention, toxicity values were measured according to the following method, taking accumulative toxicity into consideration.

Groups of 5 week oil male mice of ICR strain were used for this test, each group consisting of 10 animals. Test compounds were forcibly administered orally once a day for 7 days. The body weight of each animal was measured every day just before the adminstration. The compounds of the present invention, dissolved in polyethylene glycol 400, were administered to each testing animal in the same volume of 0.1 ml/10 g (body weight). Although the exact doses of the compounds of the invention varied depending on the particular compounds utilized, the doses were approximately within a range from 2 mg/kg to 300 mg/kg. The doses were graded into 5 rank for each testing compound. At each rank, the compound of the invention was administered to each group. On the 14th day after the completion of administration, the survival and death of the tested animals were judged and $LD_{10}$ values were calculated according to the Litchfield-Wilcoxon method.

II. RESULTS OF THE TESTS

The results of the above Tests (a) and (b) and the therapeutic indices calculated therefrom are shown in Table 1. The therapeutic indices were calculated according to the following equation:

Therapeutic index = $LD_{10}$ value ÷ T/C 0.50 value

TABLE 1

|  | Compound administered In General Formula(I), (R)$_m$ | n | Value indicating T/C 0.70(mg/K$_g$) | Value indicating T/C 0.50(mg/K$_g$) | $LD_{10}$ (mg/K$_g$) | Therapeutic index |
|---|---|---|---|---|---|---|
| Compound of the present invention | 2-methoxy | 3 | 3.6 | 10 | 36 | 3.60 |
|  | 3-methoxy | " | 2.8 | 8.3 | 19 | 2.29 |
|  | 4-methoxy | " | 2.5 | 7.6 | 17 | 2.24 |
|  | 2-ethoxy | " | 2.4 | 7.0 | 35 | 5.00 |
|  | 4-ethoxy | " | 1.2 | 5.3 | 27 | 5.09 |
|  | 4-η-propoxy | " | 1.8 | 7.4 | 24 | 3.24 |
|  | 4-η-butoxy | " | 1.0 | 4.0 | 19 | 4.75 |
|  | 2,3-dimethoxy | " | 2.0 | 8.1 | 23 | 2.84 |
|  | 3,5-dimethoxy | " | 3.0 | 9.7 | 36 | 3.71 |
|  | 2-methoxy | 4 | 2.0 | 7.6 | 17 | 2.24 |
|  | 3-methoxy | " | 2.1 | 9.5 | 26 | 2.74 |
|  | 4-methoxy | " | 0.9 | 4.2 | 12 | 2.86 |
|  | 2-ethoxy | " | 0.8 | 4.1 | 22 | 5.37 |
|  | 4-ethoxy | " | — | 2.8 | 16 | 5.71 |
|  | 4-η-propoxy | " | 1.1 | 4.3 | 20 | 4.65 |
|  | 4-η-butoxy | " | 2.4 | 8.0 | 20 | 2.50 |
|  | 2,3-dimethoxy | " | 2.3 | 8.0 | 23 | 2.88 |
|  | 3,4-Methylenedioxy | 3 | 1.8 | 7.4 | 12 | 1.62 |
|  | 3,4-Methylenedioxy | 4 | 2.7 | 7.6 | 15 | 1.97 |
| Known *Compound | A |  | 14 | 28 | 28 | 1.00 |
|  | B |  | 3.1 | 9.0 | 19 | 2.11 |

TABLE 1-continued

| Compound administered In General Formula(I), (R)$_m$ | n | Value indicating T/C 0.70(mg/K$_g$) | Value indicating T/C 0.50(mg/K$_g$) | LD$_{10}$ (mg/K$_g$) | Therapeutic index |
|---|---|---|---|---|---|
| C | | 11 | 34 | 76 | 2.24 |
| D | | 25 | 70 | 61 | 0.87 |
| E | | 9 | 37 | 43 | 1.16 |
| F | | 31 | 67 | 63 | 0.94 |

*The same tests as indicated in paragraphs (a) and (b) above were conducted using the following known similar compounds:
A: 2'-Deoxy-3',5'-di-O—n-pentanoyl-5-fluorouridine
B: 2'-Deoxy-3',5'-di-O—n-hexanoyl-5-fluorouridine
C: 3-(2,3-dimethoxybenzoyl)-2'-deoxy-3',5'-di-O—acetyl-5-fluorouridine
D: 3-(3,4-methylenedioxybenzoyl)-2'-deoxy-5-fluorouridine
E: 3-(3,4-methylenedioxybenzoyl)-2'-deoxy-3',5'-di-O—acetyl-5-fluorouridine F: 5-Fluorouracil.

As is evident from the results shown in Table 1 and Table 1 (cont'd), the compounds of the present invention exhibit strong anti-tumor activity in comparison with the known similar compounds.

In clinical chemotherapy, the compounds of the present invention are preferably administered in a daily dose of 1–600 mg. As a mode of administration, oral administration is preferably applied to the compounds of the present invention but parenteral administration such as intravenous injection or intrarectal medication by means of a suppository is also applicable.

As pharmaceutical preparations suitable for oral administration, tablets, capsules (hard capsules and soft capsules), liquids and granules each unit-containing 0.5–100 mg of the compound of the invention as the active ingredient, can be utilized. These preparations may contain, in addition to the active ingredient, other conventional auxiliary components such as milk sugar, corn starch, potato starch, various cane sugar esters of fatty acids, microcrystalline cellulose and polyethylene glycol 4000 as excipients; acacia, gelatine, hydroxypropylcellulose and potato starch as binders; magnesium stearate and talc as lubricants; and carboxymethylcellulose calcium, potato starch and corn starch as disintegrating agents. Usual solubilizing agents and suspending agents may also be contained in the preparations, with polyethylene glycol 200–600 being the particular liquid preferred. Examples of a base for suppositories include glycerin, cacao butter, glycerogelatine, polyethylene glycol and the like.

The present invention will now be illustrated in more detail by way of the following examples which are given as being exemplary of the present invention and accordingly should not be considered, in any way, as limiting the scope thereof.

EXAMPLE 1

To a solution of 4.1 g of 2'-deoxy-3',5'-di-O-n-pentanoyl-5-fluorouridine in 20 ml of dry dioxane were added 2.1 ml of triethylamine and 2.6 g of 2,3-dimethoxybenzoyl chloride. The mixture was subjected to reaction at room temperature for one hour and then at 60° C. for one hour. The reaction liquid was cooled and then concentrated under reduced pressure. The residue was dissolved in ethyl acetate and the solution was washed with a 0.1-N aqueous solution of caustic soda and then with a saturated aqueous solution of edible salt and dried with anhydrous sodium sulfate. The solvent was removed by distillation under reduced pressure and the residue was purified by column chromatography on silica gel (elution solvent: chloroform). The resultant oily substance was dissolved in about 30 ml of ethanol and the solution was treated with active carbon. The ethanol was distilled off under reduced pressure and the residue was again purified by column chromatography on silica gel (elution solvent: chloroform) whereby 4.7 g (81.0%) of 3-(2,3-dimethoxybenzoyl)-2'-deoxy-3',5'-di-O-n-pentanoyl-5-fluorouridine were obtained as an oily substance.

UV ($\lambda_{max}^{EtOH}$, nm) 265, 327.

NMR $\delta$(ppm, CDCl$_3$): Uridine moiety: 7.72 (d, H$_6$), 6.26 (broad-t, H$_1$'), near 2.4 (m, H$_2$'), 5.16–5.32 (m, H$_3$'), 4.20–4.46 (m, H$_4$', H$_5$'), 2.02–2.68 (m, 2×COCH$_2$), 1.20–1.84 (m, 4×CH$_2$), 0.82–1.06 (m, 2×CH$_3$). Benzoyl moiety: 7.50–7.62 (m, H$_6$), 7.10–7.22 (m, H$_4$, H$_5$), 3.88 (s, CH$_3$O), 3.86 (s, CH$_3$O).

Elementary analysis (as C$_{28}$H$_{35}$FN$_2$O$_{10}$): Calc. (%): C 58.13; H 6.10; N 4.84. Found (%): C 57.85; H 6.20; N 4.67.

EXAMPLES 2–4

In the same manner as described in Example 1, 2'-dioxy-3',5'-di-O-alkylcarbonyl-5-fluorouridine derivatives were prepared. The structures, yields and physical characteristics of the prepared derivatives are shown in Table 2.

TABLE 2

| Example No. | In General Formula (1) (R)m (n) | Yield (%) Nature | Elementary Analysis Empirical formula Calc. (%):C,H,N Found (%):C,H,N | UV $\lambda^{EtOH}$ max (nm) | NMR (CDCl$_3$) $\delta$(ppm) Uridine moiety | | Benzoyl moiety |
|---|---|---|---|---|---|---|---|
| 2 | 2-ethoxy (3) | 85.0 Oily substance | C$_{28}$H$_{35}$FN$_2$O$_9$ 59.78 6.27 4.98 59.92 64.4 5.04 | 259 324 | 7.69(d,H$_6$) near 2.4(m,H'$_2$) 4.18–4.54(m,H'$_4$,H'$_5$) 1.12–1.82(m,4 × CH$_2$) | 6.28(broad-t,H'$_1$) 5.14–5.30(m,H'$_3$) 2.00–2.64(m,2 × COCH$_2$) 0.80–1.06(m,2 × CH$_3$) | 8.09(dd,H$_6$) 7.55(td,H$_4$) 7.04(t,H$_5$) 6.92(d,H$_3$) 4.02(q,CH$_2$O) 1.26(t,CH$_3$) |
| 3 | 2,3-dimethoxy(4) | 71.2 Oily substance | C$_{30}$H$_{39}$FN$_2$O$_{10}$ 59.40 6.48 4.62 58.89 6.50 4.35 | 213 265 326 | 7.74(d,H$_6$) near 2.4(m,H'$_2$) 4.20–4.46(m,H'$_4$,H'$_5$) 1.20–1.78(m,6 × CH$_2$) | 6.26(broad-t,H'$_1$) 5.16–5.30(m,H'$_3$) 2.10–2.64(m,2 × COCH$_2$) 0.78–1.02(m,2 × CH$_3$) | 7.48–7.60 (m,H$_6$) 7.08–7.22 (m,H$_4$,H$_5$) 3.86(s,2 × CH$_3$O) |
| 4 | 4-methoxy(3) | 79.0 | C$_{27}$H$_{33}$FN$_2$O$_9$ | 220 | 7.73(d,H$_6$) | 6.23(broad-t,H'$_1$) | 7.84(d,H$_2$,H$_6$) |

TABLE 2-continued

| Example No. | In General Formula (1) (R)m (n) | Yield (%) Nature | Elementary Analysis Empirical formula Calc. (%):C,H,N Found (%):C,H,N | UV $\lambda_{max}^{EtOH}$ (nm) | NMR (CDCl$_3$) δ(ppm) | | |
|---|---|---|---|---|---|---|---|
| | | | | | | Uridine moiety | Benzoyl moiety |
| | | Oily sub- | 59.12 6.06 5.11<br>58.89 6.23 4.98 | 286 | near 2.4(m,H'$_2$)<br>4.16–4.54(m,H'$_4$,H'$_5$)<br>1.12–1.80(m,4 × CH$_2$) | 5.12–5.28(m,H'$_3$)<br>2.00–2.62(m,2 × COCH$_2$)<br>0.78–1.04(m,2 × CH$_3$) | 6.93(d,H$_3$,H$_5$)<br>3.86(s,CH$_3$O) |

EXAMPLE 5

To a solution of 2.0 g of 2'-deoxy-3',5'-di-O-n-hexanoyl-5-fluorouridine in 30 ml of chloroform were added 0.95 ml of triethylamine and 1.08 g of 4-n-propoxybenzoyl chloride. The mixture was subjected to reaction at room temperature for one hour and then at 50°–60° C. for 30 minutes. The reaction liquid was cooled and washed with a 0.1-N aqueous solution of caustic soda and then with a saturated aqueous solution of edible salt and dried with anhydrous sodium sulfate. The solvent was removed by distillation under reduced pressure and the residue was purified by column chromatography on silica gel (elution solvent: chloroform). The resultant purified oily substance was dried at room temperature under reduced pressure whereby 2.1 g (77.8%) of 3-(4-n-propoxybenzoyl)-2'-deoxy-3',5'-di-O-n-hexanoyl-5-fluorouridine were obtained as an oily substance.

UV ($\lambda_{max}^{EtOH}$, nm): 220, 288.

NMR δ(ppm, CDCl$_3$): Uridine moiety: 7.78 (d, H$_6$), 6.24 (broad-t, H$_1$'), near 2.4 (m, H$_2$'), 5.16–5.28 (m, H$_3$'), 4.24–4.52 (m, H$_4$', H$_5$'), 2.24–2.46 (m, 2×COCH$_2$), 1.20–1.92 (m, 6×CH$_2$), 0.82–1.10 (m, 2×CH$_3$). Benzoyl moiety: 7.86 (d, H$_2$, H$_6$), 6.92 (d, H$_3$, H$_5$), 3.99 (t, CH$_2$O), near 1.7 (m, CH$_2$), near 1.0 (m, CH$_3$).

Elementary analysis (as C$_{31}$H$_{41}$FN$_2$O$_9$): Calc. (%): C 61.58; H 6.83; N 4.63. Found (%): C 61.35; H 6.98; N 4.43.

EXAMPLE 6

To a solution of 2.0 g of 2'-deoxy-3',5'-di-O-n-pentanoyl-5-fluorouridine in 30 ml of chloroform were added 1.0 ml of triethylamine and 0.98 g of 2-methoxybenzoyl chloride. The mixture was subjected to reaction at room temperature for 5 hours. The reaction liquid was treated in the same manner as described in Example 5 whereby 2.1 g (79.8%) of 3-(2-methoxybenzoyl)-2'-deoxy-3',5'-di-O-pentanoyl-5-fluorouridine were obtained as an oily substance.

UV ($\lambda_{max}^{EtOH}$, nm): 259, 322.

NMR δ(ppm, CDCl$_3$): Uridine moiety: 7.69 (d, H$_6$), 6.16 (broad-t, H$_1$'), near 2.4 (m, H$_2$'), 5.14–5.28 (m, H$_3$'), 4.18–4.40 (m, H$_4$', H$_5$'), 2.18–2.46 (m, 2×COCH$_2$), 1.14–1.80 (m, 4×CH$_2$), 0.84–0.98 (m, 2×CH$_3$). Benzoyl moiety: 8.06 (dd, H$_6$), 7.52 (td, H$_4$), 7.04 (t, H$_5$), 6.92 (d, H$_3$), 3.78 (s, CH$_3$O).

Elementary analysis (as C$_{27}$H$_{33}$FN$_2$O$_9$): Calc. (%): C 59.12; H 6.06; N 5.11. Found (%): C 58.68; H 6.02; N 4.80.

EXAMPLE 7

To a solution of 2.0 g of 2'-deoxy-3',5'-di-O-n-pentanoyl-5-fluorouridine in 30 ml of chloroform were added 1.0 ml of triethylamine and 1.2 g of 2,3-dimethoxybenzoyl chloride. The mixture was subjected to reaction at room temperature for 30 minutes and then at 50°–60° C. for 2 hours. The reaction liquid was cooled and then treated in the same manner as described in Example 5 whereby 4.6 (79.3%) of 3-(2,3-dimethoxybenzoyl)-2'-deoxy-3',5'-di-O-n-pentanoyl-5-fluorouridine were obtained as an oily substance. The physical characteristics of this substance were identical with those of the oily substance obtained in Example 1.

EXAMPLE 8

To a solution of 4.1 g of 2'-deoxy-3',5'-di-O-n-pentanoyl-5-fluorouridine in 10 ml of pyridine were added 4.3 g of 4-n-butoxybenzoyl chloride. The mixture was subjected to reaction at 50°–60° C. for 12 hours. The reaction liquid was concentrated under reduced pressure. The residue was dissolved in ethyl acetate and the solution was washed with a saturated aqueous solution of edible salt and dried with anhydrous sodium sulfate. The solvent was removed by distillation under reduced pressure and the residue was subjected, as in Example 1, to column chromatography and treatment with active carbon whereby 4.6 g (78.0%) of 3-(4-n-butoxybenzoyl)-2'-deoxy-3',5'-di-O-n-pentanoyl-5-fluorouridine were obtained as an oily substance.

UV ($\lambda_{max}^{EtOH}$, nm): 221, 289.

NMR δ(ppm, CDCl$_3$): Uridine moiety: 7.76 (d, H$_6$), 6.27 (broad-t, H$_1$'), near 2.4 (m, H$_2$'), 5.16–5.32 (m, H$_3$'), 4.20–4.58 (m, H$_4$', H$_5$'), 2.04–2.69 (m, 2×COCH$_2$), 1.15–1.96 (m, 4×CH$_2$), 0.82–1.12 (m, 2×CH$_3$). Benzoyl moiety: 7.88 (d, H$_2$, H$_6$), 6.95 (d, H$_3$, H$_5$), 4.06 (t, CH$_2$O), near 1.7 (m, 2×CH$_2$), near 1.0 (m, CH$_3$).

Elementary analysis (as C$_{30}$H$_{39}$FN$_2$O$_9$): Calc. (%): C 61.01; H 6.66; N 4.74. Found (%): C 61.00; H 6.74; N 5.16.

EXAMPLE 9

To a solution of 4.1 g of 2'-deoxy-3',5'-di-O-n-pentanoyl-5-fluorouridine in 20 ml of dioxane were added, under ice cooling; 2.1 ml of triethylamine and 2.1 g of 4-n-butoxybenzoyl chloride. The mixture was subjected to reaction at room temperature for 30 minutes and then at 50°–60° C. for 2 hours. The reaction liquid was treated in the same manner as described in Example 1 whereby 5.0 g (84.6%) of 3-(4-n-butoxybenzoyl)-2'-deoxy-3',5'-di-O-n-pentanoyl-5-fluorouridine were obtained as a oily substance. The physical characteristics of this substance were identical with those of the oily substance obtained in Example 8.

EXAMPLE 10

To a solution of 2.0 g of 2'-deoxy-3',5'-di-O-n-hexanoyl-5-fluorouridine in 40 ml of diethyl ether were added 0.95 ml of triethylamine and 0.93 of 3-methoxybenzoyl chloride. The mixture was subjected to reaction at room temperature for 10 hours. The reaction liquid was cooled and then treated in the same manner as described in Example 5 whereby 1.6 g (61.5%) of 3-(3-methoxybenzoyl)-2'-deoxy-3',5'-di-O-n-hexanoyl-5-fluorouridine were obtained as an oily substance.

UV ($\lambda_{max}^{EtOH}$, nm); 220, 261, 318.

NMR δ(ppm, CDCl$_3$): Uridine moiety: 7.76 (d, H$_6$), 6.24 (broad-t, H$_1$'), near 2.4 (m, H$_2$'), 5.14–5.28 (m, H$_3$'), 4.26–4.44 (m, H$_4'$, H$_5'$), 2.18–2.50 (m, 2×COCH$_2$), 1.20–1.74 (m, 6×CH$_2$), 0.82–0.96 (m, 2×CH$_3$). Benzoyl moiety: 7.12–7.50 (m, aromatic H), 3.86 (s, CH$_3$O).

Elementary analysis (as C$_{29}$H$_{37}$FN$_2$O$_9$): Calc. (%): C 60.41; H 6.47; N 4.86. Found (%): C 60.15; H 6.52; N 4.71.

EXAMPLE 11

To a solution of 4.4 g of 2'-deoxy-3',5'-di-O-n-hexanoyl-5-fluorouridine in 30 ml of acetonitrile were added 3.5 ml of triethylamine and 3.4 g of 4-methoxybenzoyl chloride. The mixture was subjected to reaction at room temperature for 6 hours. The reaction liquid was concentrated under reduced pressure and the residue was dissolved in ethyl acetate. The ethyl acetate solution was treated in the same manner as described in Example 5 whereby 4.5 g (78.0%) of 3-(4-methoxybenzoyl)-2'-deoxy-3',5'-di-O-n-hexanoyl-5-fluorouridine were obtained as an oily substance.

UV ($\lambda_{max}^{EtOH}$, nm): 221, 287.

NMR $\delta$ (ppm, CDCl$_3$): Uridine moiety: 7.75 (d, H$_6$), 6.24 (broad-t, H$_1'$), near 2.4 (m, H$_2'$), 5.08–5.34 (m, H$_3'$), 4.18–4.54 (m, H$_4'$, H$_5'$), 2.04–2.64 (m, 2×COCH$_2$), 1.16–1.90 (m, 6×CH$_2$), 0.76–1.06 (m, 2×CH$_3$). Benzoyl moiety: 7.87 (d, H$_2$, H$_6$), 6.93 (d, H$_3$, H$_5$), 3.86 (s, CH$_3$O).

Elementary analysis (as C$_{29}$H$_{37}$FN$_2$O$_9$): Calc. (%): C 60.41; H 6.47; N 4.86. Found (%): C 60.78; H 6.59; N 4.69.

EXAMPLE 12

To a solution of 4.4 g of 2'-deoxy-3',5'-di-O-n-hexanoyl-5-fluorouridine in 30 ml of acetonitrile were added 3.5 ml of triethylamine and 4.0 g of 2,3-dimethoxybenzoyl chloride. The mixture was subjected to reaction at room temperature for 2 hours and then at 50°–60° C. for one hour. The reaction liquid was concentrated under reduced pressure and the residue was dissolved in ethyl acetate. The ethyl acetate solution was treated in the same manner as described in Example 5 whereby 3.9 g (64.3%) of 3-(2,3-dimethoxybenzoyl)-2'-deoxy-3',5'-di-O-n-hexanoyl-5-fluorouridine were obtained as an oily substance. The physical characteristics of this substance were identical with those of the oily substance obtained in Example 3.

EXAMPLE 13

To a solution of 4.4 g of 2'-deoxy-3',5'-di-O-n-hexanoyl-5-fluorouridine in 20 ml of dioxane were added 2.1 ml of triethylamine and 2.2 g of 4-n-propoxybenzoyl chloride. The mixture was subjected to reaction at room temperature for 30 minutes and then at 60° C. for 30 minutes. The reaction liquid was cooled and then concentrated under reduced pressure. The residue was dissolved in ethyl acetate and the solution was washed with a 0.1-N aqueous solution of caustic soda and then with a saturated aqueous solution of edible salt and dried with anhydrous sodium sulfate. The solvent was removed by distillation under reduced pressure and the residue was purified by column chromatography on silica gel (elution solvent: chloroform). The resultant purified oily substance was dried at room temperature under reduced pressure whereby 5.1 g (84.3%) of 3-(4-n-propoxybenzoyl-2'-deoxy-3',5'-di-O-n-hexanoyl-5-fluorouridine were obtained as an oily substance. The physical characteristics of this substance were identical with those of the oily substance obtained in Example 5.

EXAMPLES 14–21

In the same manner as described in Example 13, 2'-deoxy-3',5'-di-O-alkylcarbonyl-5-fluorouridine derivatives are prepared. The structures, yields and physical characteristics of the prepared derivatives are shown in Table 3.

TABLE 3

| Example No. | In General Formula (I) (R)m (n) | Yield (%) Nature | Elementary Analysis Empirical formula Calc.(%):C,H,N Found(%):C,H,N | UV $\lambda^{EtOH}$ max (nm) | NMR (CDCl$_3$) $\delta$ (ppm) Uridine moiety | | Benzoyl moiety |
|---|---|---|---|---|---|---|---|
| 14 | 3,5-dimethoxy(3) | 71.3 Oily substance | C$_{28}$H$_{35}$FN$_2$O$_{10}$ 58,13 6.10 4.84 57.91- 6.25 5.09 335 | 217 274 4.20–4.44(m,H'$_4$H'$_5$) | 7.76(d,H$_6$) near 2.4 (m,H'$_2$) 2.16–2.52(m,2 × COCH$_2$) 1.16–1.76(m,4 × CH$_2$) | 6.24(broad-t,H'$_1$) 5.15–5.30(m,H'$_3$) 3.82(s,2 × CH$_3$O) 0.80–1.04(m,2 × CH$_{32}$) | 6.96–7.08 (m,H$_2$,H$_6$) 6.68–6.76 (m,H$_4$) |
| 15 | 4-ethoxy(4) | 79.8 Oily substance | C$_{30}$H$_{39}$FN$_2$O$_9$ 61.01 6.66 4.74 60.82 6.84 4.98 | 220 289 | 7.76(d,H$_6$) near 2.4 (m,H'$_2$) 4.22–4.58(m,H'$_4$,H'$_5$) 1.14–1.86(m,6 × CH$_2$) | 6.28(broad-t,H'$_1$) 5.14–5.32(m,H'$_3$) 2.04–2.68(m,2 × COCH$_2$) 0.76–1.04(m,2 × CH$_3$) | 7.88(d,H$_2$,H$_6$) 6.95(d,H$_3$,H$_5$) 4.13(q,CH$_2$O) near 1.4 (m,CH$_3$) |
| 16 | 4-n-butoxy(4) | 78.0 Oily substance | C$_{32}$H$_{43}$FN$_2$O$_9$ 62.12 7.00 453 62.27 7.38 4.78 | 220 289 | 7.75(d,H$_6$) near 2.4(m,H'$_2$) 4.22–4.60(m,H'$_4$,H'$_5$) 1.16–1.92(m,6 × CH$_2$) | 6.29(broad-t,H'$_1$) 5.16–5.34(m,H'$_3$) 2.06–2.70(m,2 × COCH$_2$) 0.80–1.16(m,2 × CH$_3$) | 7.87(d,H$_2$,H$_6$) 6.95(d,H$_3$,H$_5$) 4.07(t,CH$_2$O) near 1.7 (m,2 × CH$_2$) near 1.0 (m,CH$_3$) |
| 17 | 2-methoxy(4) | 78.5 Oily substance | C$_{29}$H$_{37}$FN$_2$O$_9$ 60.41 6.47 4.86 60.51 6.17 4,87 | 259 322 | 7.69(d,H$_6$) near 2.4(m,H'$_1$) 4.18–4.52(m,H'$_4$,H'$_5$) 1.14–1.80(m,6 × CH$_2$) | 6.16(broad-t,H'$_1$) 5.14–5.30(m,H'$_3$) 2.14–2.44(m,2 × COCH$_2$) 0.80–0.96(m,2 × CH$_3$) | 8.06(dd,H$_6$) 7.52(td,H$_4$) 7.03(t,H$_5$) 6.92 (d,H$_3$) 3.76(s,CH$_3$O) |
| 18 | 3-methoxy(3) | 71.0 Oily substance | C$_{27}$H$_{33}$FN$_2$O$_9$ 59.12 6.06 5.11 59.26 6.16 5.40 | 220 261 318 | 7.76(d,H$_6$) near 2.4(m,H'$_2$) 4.24–4.46(m,H'$_4$,H'$_5$) 1.12–1.80(m,4 × CH$_2$) | 6.25(broad-t,H'$_1$) 5.15–5.30(m,H'$_3$) 2.18–2.46(m,2 × COCH$_2$) 0.82–1.02(m,2 × CH$_3$) | 7.12–7.48 (m,aromatic H) 3.86(s,CH$_3$O) |
| 19 | 2-ethoxy(4) | 61.5 | C$_{30}$H$_{39}$FN$_2$O$_9$ | 259 | 7.69(d,H$_6$) | 6.28(broad-t,H'$_1$) | 8.09(dd,H$_6$) |

TABLE 3-continued

| Example No. | In General Formula (I) (R)m (n) | Yield (%) Nature | Elementary Analysis Empirical formula Calc.(%):C,H,N Found(%):C,H,N | UV $\lambda_{max}^{EtOH}$ (nm) | NMR (CDCl$_3$) $\delta$ (ppm) Uridine moiety | | NMR (CDCl$_3$) $\delta$ (ppm) Benzoyl moiety |
|---|---|---|---|---|---|---|---|
| | | Oily substance | 61.01 6.66 4.74<br>61.22 6.84 4.56 | 324 | near 2.4(m,H'$_2$)<br>4.18–4.54(m,H'$_4$,H'$_5$)<br>1.14–1.86(m,6 × CH$_2$) | 5.15–5.30(m,H'$_3$)<br>2.04–2.68(m,2 × COCH$_2$)<br>0.80–1.04(m,2 × CH$_3$) | 7.55(td,H$_4$)<br>7.04(t,H$_5$)<br>6.92(d,H$_3$)<br>4.02(q,CH$_2$O)<br>near 1.3 (m,CH$_3$) |
| 20 | 4-ethoxy(3) | 73.3 Oily substance | C$_{20}$H$_{36}$FN$_2$O$_9$<br>59.78 6.27 4.98<br>59.61 6.27 5.21 | 220<br>288 | 7.76(d,H$_6$)<br>near 2.4(m,H'$_2$)<br>4.20–4.56(m,H'$_4$,H'$_5$)<br>1.12–1.82(m,4 × CH$_2$) | 6.28(broad-t,H'$_1$)<br>5.14–5.30(m,H'$_3$)<br>2.04–2.68(m,2 × COCH$_2$)<br>0.78–1.06(m,2 × CH$_3$) | 7.88(d,H$_2$,H$_6$)<br>6.95(d,H$_3$,H$_5$)<br>4.14(q,CH$_2$O)<br>1.35(t,CH$_3$) |
| 21 | 4-n-propoxy(3) | 76.4 Oily substance | C$_{29}$H$_{37}$FN$_2$O$_9$<br>60.41 6.47 4.86<br>60.73 6.21 4.89 | 220<br>289 | 7.78(d,H$_6$)<br>near 2.4 (m,H'$_2$)<br>4.20–4.58(m,H'$_4$,H'$_5$)<br>1.16–1.96(m,4 × CH$_2$) | 6.26(broad-t,H'$_1$)<br>5.16–5.28(m,H'$_3$)<br>2.25–2.46(m,2 × COCH$_2$)<br>0.82–1.10(m,2 × CH$_3$) | 7.86(d,H$_2$,H$_6$)<br>6.92(d,H$_3$,H$_5$)<br>4.00(t,CH$_2$O)<br>near 1.7 (m,CH$_2$)<br>near 1.0 (m,CH$_3$) |

EXAMPLE 22

Using 2'-deoxy-3',5'-di-n-O-hexanoyl-5-fluorouridine and 4-methoxybenzoyl chloride, the reaction and after-treatments were carried out in the same manner as described in Example 11. The resultant oily substance was recrystallized from ethanol whereby 3-(4-methoxybenzoyl)-2'-deoxy-3',5'-di-O-n-hexanoyl-5-fluorouridine having a melting point of 81°–82° C. was obtained (yield: 75.0%) as white needle crystals.

UV ($\lambda_{max}^{EtOH}$, nm): 221, 287.

NMR $\delta$ (ppm, CDCl$_3$): Uridine moiety: 7.75 (d, H$_6$), 6.24 (broad-t, H$_1$'), near 2.4 (m, H$_2$'), 5.08–5.34 (m, H$_3$'), 4.18–4.54 (m, H$_4$', H$_5$'), 2.04–2.64 (m, 2×COCH$_2$), 1.16–1.90 (m, 6×CH$_2$), 0.76–1.06 (m, 2×CH$_3$). Benzoyl moiety: 7.87 (d, H$_2$, H$_6$), 6.93 (d, H$_3$, H$_5$), 3.86 (s, CH$_3$O).

Elementary analysis (as C$_{29}$H$_{37}$FN$_2$O$_9$): Calc. (%): C 60.41; H 6.47; N 4.86. Found (%): C 60.30; H 6.73; N 4.80.

EXAMPLES 23–25

The oily substances obtained in Examples 4, 15 and 20 were recrystallized from ethanol in the same manner as described in Example 22 whereby 3-(4-methoxybenzoyl)-2'-deoxy-3',5'-di-O-n-pentanoyl-5-fluorouridine haing a melting point of 84°–85° C. (yield: 74.0%), 3-(4-ethoxybenzoyl)-2'-deoxy-3',5'-di-O-n-hexanoyl-5-fluorouridine having a melting point of 90°–91° C. (yield: 75.0%) and 3-(4-ethoxybenzoyl)-2'-deoxy-3',5'-di-O-n-pentanoyl-5-fluorouridine having a melting point of 88°–89° C. (yield: 86.0%) were obtained, respectively, as white needle crystals. The physical characteristics of these substances were identical to UV-absorption spectra, NMR spectra and elementary analytical data with those of the corresponding oily substances obtained in Examples 4, 15 and 20.

EXAMPLE 26

To a solution of 3.0 g of 2'-deoxy-3',5'-di-O-n-pentanoyl-5-fluorouridine in 30 ml of dry dioxane were added 2.0 ml of triethylamine and 1.6 g of 3,4-methylenedioxybenzoyl chloride. The mixture was subjected to reaction at 70° C. for one hour. The reaction liquid was cooled and then concentrated under reduced pressure. The residue was dissolved in ethyl acetate and the solution was washed with a 0.1-N aqueous solution of caustic soda and then with a saturated aqueous solution of edible salt and dried with anhydrous sodium sulfate. The solvent was removed by distillation under reduced pressure and the residue was dissolved in a small amount of chloroform and filtered to remove insoluble matter. The filtrate was purified by column chromatography on silica gel (elution solvent: chloroform) whereby 1.2 g (29.0%) of 3-(3,4-methylenedioxybenzoyl)-2'-deoxy-3',5'-di-O-n-pentanoyl-5-fluorouridine were obtained as an oily substance.

UV ($\lambda_{max}^{EtOH}$, nm): 206, 236, 278, 321.

NMR $\delta$ (ppm, CDCl$_3$): Uridine moiety: 7.78 (d, H$_6$), 6.28 (broad-t, H$_1$'), near 2.4 (m, H$_2$'), 5.18–5.32 (m, H$_3$'), 4.24–4.56 (m, H$_4$', H$_5$'), 2.20–2.52 (m, 2×COCH$_2$), 1.18–1.84 (m, 4×CH$_2$), 0.88–1.00 (m, 2×CH$_3$). Benzoyl moiety: 7.52 (dd, H$_6$), 7.38 (d, H$_5$), 6.86 (d, H$_2$), 6.08 (s, CH$_2$).

EXAMPLE 27

Using 2'-deoxy-3',5'-di-O-n-hexanoyl-5-fluorouridine and 3,4-methylenedioxybenzoyl chloride, the reaction and after-treatments were carried out in the same manner as described in Example 26 whereby 1.3 g (32.0%) of 3-(3,4-methylenedioxybenzoyl)-2'-deoxy-3',5'-di-O-n-hexanoyl-5-fluorouridine were obtained.

UV ($\lambda_{max}^{EtOH}$, nm): 206, 236, 278, 321.

NMR $\delta$ (ppm, CDCl$_3$): Uridine moiety: 7.74 (d, H$_6$), 6.26 (broad-t, H$_1$'), 5.18–5.28 (m, H$_3$'), 4.24–4.42 (m, H$_4$', H$_5$'), 2.18–2.50 (m, 2×COCH$_2$), 1.18–1.76 (m, 6×CH$_2$), 0.82–0.98 (m, 2×CH$_3$). Benzoyl moiety: 7.50 (dd, H$_6$), 7.36 (d, H$_5$), 6.86 (d, H$_2$), 6.06 (s, CH$_2$).

The preparation of the anti-tumor agents of the present invention will now be illustrated in more detail by way of the following typical preparation examples:

(A) Hard capsule preparations

| Recipe 1: | |
|---|---|
| 3-(4-methoxybenzoyl)-2'-deoxy-3',5'-di-O—n-hexanoyl-5-fluorouridine | 100 mg |
| milk sugar | 160 mg |
| crystalline celulose | 27 mg |
| hydroxypropylcellulose of a low degree of substitution | 10 mg |
| magnesium stearate | 3 mg |
| Total | 300 mg |

Capsules (No. 2) are formed according to a conventional method so that each capsule may contain the above dose of ingredients. In general 3-9 capsules per day can be administered orally to adult patients.

| Recipe 2: | |
|---|---|
| 3-(4-methoxybenzoyl)-2'-deoxy-3',5'-di-O—n-hexanoyl-5-fluorouridine | 80 mg |
| cane sugar esters of fatty acids | 20 mg |
| milk sugar | 165 mg |
| crystalline cellulose | 24 mg |
| hydroxypropylcellulose of a low degree of substitution | 8 mg |
| magnesium stearate | 3 mg |
| Total | 300 mg |

Capsules are formed according to a conventional method so that each capsule may contain the above dose of ingredients. In general, 3-9 capsules can be administered orally to adult patients.

| Recipe 3: | |
|---|---|
| The compound of the present invention | 80 mg |
| milk sugar | 161 mg |
| polyethylene glycol 6000 | 20 mg |
| crystalline cellulose | 21 mg |
| hydroxypropyl cellulose | 8 mg |
| carboxymethyl cellulose calcium | 5 mg |
| talc | 5 mg |
| Total | 300 mg |

The following compounds can be used as the compound of the present invention for the above recipe:
3-(4-methoxybenzoyl-2'-deoxy-3',5'-di-O-n-hexanoyl-5-fluorouridine
3-(4-ethoxybenzoyl)-2'-deoxy-3',5'-di-O-n-pentanoyl-5-fluorouridine First, granules are formed according to a usual method, using the compound of the present invention, polyethylene glycol 6000, milk sugar, crystalline cellulose and hydroxypropylcellulose. The granules are then incorporated with carboxymethylcellulose and talc and the mixture is worked up according to a conventional method to capsules (No. 2) in such a manner that each capsule may contain the above dose of ingredients. As a rule, 3-9 capsules per day can be administered orally to adult patients.

(B) Soft capsule preparations

| Recipe: | |
|---|---|
| The compound of the present invention | 50 mg |
| polyethylene glycol 400 | 250 mg |
| propylene glycol | 10 mg |
| bleached beeswax | 10 mg |
| Total | 320 mg |

The following compounds can be used as the compound of the present invention for the above recipe:
3-(4-methoxybenzoyl)-2'-deoxy-3',5'-di-O-n-hexanoyl-5-fluorouridine
3-(4-n-propoxybenzoyl)-2'-deoxy-3',5'-di-O-n-pentanoyl-5-fluorouridine Capsules are formed according to a conventional method so that each capsule may contain the above dose of ingredients. As a rule, 3-9 capsules per day can be administered orally.

(C) Syrup preparations (1) A vial containing the following ingredients is prepared.

| 3-(4-methoxybenzoyl)-2'-dexoy-3',5'-di-O—n-hexanoyl-5-fluorouridine | 10 mg |
|---|---|
| Carboxymethylcellulose calcium | 4 mg |
| white sugar | 486 mg |
| Total | 500 mg |

(2) An ampoule containing the following ingredients is prepared

| polyethylene glycol 400 | 3000 mg |
|---|---|
| purified water | 1000 mg |
| Total | 4000 mg |

On oral administration, the solution in the ampoule (2) is added to the vial (1) and the mixture is shaken well. The resultant syrup corresponds to a unit dose and can be administered orally 3-9 times per day.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An ester derivative of alkoxybenzoyldeoxyfluorouridine of the general formula:

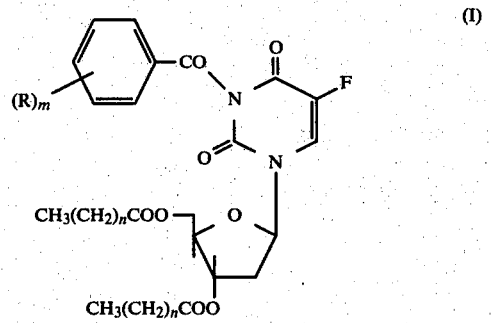

(I)

wherein R is an alkoxy group having 1 to 4 carbon atoms, m is 1 or 2, and n is 3 or 4, and when m is 2, the adjacent two R's may be combined to form an alkylenedioxy group as a whole.

2. The ester derivative of alkoxybenzoyldeoxyfluorouridine according to claim 1, wherein R is a methoxy group.

3. The ester derivative of alkoxybenzoyldeoxyfluorouridine according to claim 1, wherein R is an ethoxy group.

4. The ester derivative of alkoxybenzoyldeoxyfluorouridine according to claim 1, wherein R is a propoxy group.

5. The ester derivative of alkoxybenzoyldeoxyfluorouridine according to claim 1, wherein R is a butoxy group.

6. A pharmaceutical composition containing as an active ingredient an effective anti-tumor amount of an ester derivative of alkoxybenzoyldeoxyfluorouridine of the general formula:

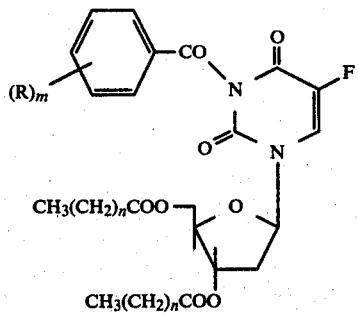

wherein R is an alkoxy group having 1 to 4 carbon atoms, m is 1 or 2, and n is 3 or 4, and when m is 2, the adjacent two R's may be combined to form an alkylenedioxy group as a whole and a pharmaceutically acceptable carrier or diluent.

7. A pharmaceutical composition according to claim 6, wherein R is a methoxy group.

8. A pharmaceutically composition according to claim 6, wherein R is an ethoxy group.

9. A pharmaceutical composition according to claim 6, wherein R is a propoxy group.

10. A pharmaceutical composition according to claim 6, wherein R is a butoxy group.

11. A pharmaceutical composition according to claim 6, wherein the carrier is polyethylene glycol or cane sugar esters of fatty acids.

12. A pharmaceutical composition as in claim 6, wherein R is ethoxy and m is 1.

13. A pharmaceutical composition as in claim 6 wherein R is propoxy and m is 1.

14. A pharmaceutical composition as in claim 6, wherein R is butoxy and m is 1.

15. A pharmaceutical composition as in claim 6, wherein R is methoxy, m is 2, n is 4 and the two methoxy groups are combined to form a methylenedioxy group.

* * * * *